(12) United States Patent
Vrba et al.

(10) Patent No.: US 7,118,539 B2
(45) Date of Patent: Oct. 10, 2006

(54) ARTICULATING GUIDE WIRE FOR EMBOLIC PROTECTION AND METHODS OF USE

(75) Inventors: Anthony C. Vrba, Maple Grove, MN (US); Alan Eskuri, Hanover, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 591 days.

(21) Appl. No.: 10/083,288

(22) Filed: Feb. 26, 2002

(65) Prior Publication Data

US 2003/0163064 A1 Aug. 28, 2003

(51) Int. Cl.
*A61B 5/00* (2006.01)
*A61M 25/00* (2006.01)
*A61M 29/00* (2006.01)

(52) U.S. Cl. .................................................. 600/585
(58) Field of Classification Search ................ 600/585, 600/434; 606/159, 167, 200, 127, 113, 114, 606/180, 110, 128, 179; 604/22, 93.01, 96.01, 604/249, 528, 908
See application file for complete search history.

(56) References Cited

U.S. PATENT DOCUMENTS

| | | | |
|---|---|---|---|
| 3,472,230 A | 10/1969 | Fogarty | |
| 3,841,308 A * | 10/1974 | Tate | ............................ 600/585 |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,842,579 A | 6/1989 | Shiber | |
| 4,873,978 A | 10/1989 | Ginsburg | |
| 4,921,478 A | 5/1990 | Solano et al. | |

(Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent-Ischemic Stroke," The New England Journal of Medicine, pp. 1216-1221 (May 1996).

(Continued)

*Primary Examiner*—Max F. Hindenburg
*Assistant Examiner*—Brian Szmal
(74) *Attorney, Agent, or Firm*—Crompton, Seager & Tufte LLC (57) ABSTRACT

An intravascular guidewire having an articulating distal section for improved maneuverability beyond a lesion or other protrusion within a body lumen. An elongated core wire having an actuatable stop disposed thereon is adapted to have a reduced profile in a first position, and an enlarged profile in a second position. The actuatable stop can be adapted to expand by any number of means, including a spring coil, a polymeric tube or a mesh sleeve. In one particular embodiment, the actuatable stop comprises a distal section of a tubular member having a plurality of circumferentially disposed openings adapted to permit a plurality of struts disposed therebetween to expand in an outward direction when compressed axially.

29 Claims, 6 Drawing Sheets

U.S. PATENT DOCUMENTS

| | | |
|---|---|---|
| 4,921,484 A | 5/1990 | Hillstead |
| 4,926,858 A | 5/1990 | Giffort, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,167,239 A * | 12/1992 | Cohen et al. ............... 600/585 |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,602,265 B1 * | 8/2003 | Dubrul et al. ............... 606/159 |
| 2002/0128678 A1 | 9/2002 | Petersen |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 486 157 A2 | 10/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |

| | | |
|---|---|---|
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Emboloic Potential of Intraaortic Atherosclerotic Debris," American College of Cardiology (Jan. 1991).

Cragg, Andrew et al., "A New Percutaneous Vena Cava Filger," *AJR*, *141*:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, *64*(3):634-639 (Sep. 1968).

Haissaguerre et al., "Spontaneous Initiation of Atrial Fibrillation by Ectopic Beats Originating in the Pulmonary Veins," *The New England Journal of Medicine*, *339*(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patency of Ductus Arteriosus After Balloon Dilation: an Experimental Study," *Laboratory Investigation*, *69*(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, *31*:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, *14*(2):English Abstract Only (Apr. 1994).

Onal et al., "Primary Stenting for Complex Atherosclerotic Plaques in Aortic and Iliac Stenoses," *Cardiovascular & Interventional Radiology*, *21*(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* *120*(3):658-660 (Sep. 1990).

Waksman et al., "Distal Embolization is Common After Directional Atherectomy . . . ," *American Heart Journal*, *129*(3):430-435 (1995).

Wholey, Mark H. et al., PTA and stents in the Treatment of Extracranial Circulation, *The Journal of Invasive Cardiology*, *8*(E):25E-30E (1996).

\* cited by examiner

ARTICULATING GUIDE WIRE FOR EMBOLIC PROTECTION AND METHODS OF USE

FIELD OF THE INVENTION

The present invention relates generally to the field of intravascular guidewires. More particularly, the present invention pertains to intravascular guidewires having an articulating distal section.

BACKGROUND OF THE INVENTION

The use of guidewires or core wires in conjunction with intravascular devices such as embolic protection filters or catheters is widely known. Typically, a flexible guidewire is inserted into a vascular lumen through a guide catheter, and then advanced to a desired location within the body. Once the guidewire is in place, an intravascular device such as an embolic filter can be advanced along the guidewire distal a lesion and deployed to prevent embolic debris from flowing downstream during, for example, an angioplasty or atherectomy procedure.

To facilitate steering and tracking through the tortuous vascular system, it is desirable to have a radially flexible guidewire capable of traversing the cavities of the body by applying a force on a proximal section of the guidewire. It is also desireable for the distal section of the guidewire to have a reduced profile capable of placement beyond a lesion or other protrusion in the vasculature with minimal interference. One such series of improvements has resulted in the use of a thin, flexible guidewire having a distally tapering cross-sectional area for improved steering, and a coiled wire helix disposed about an arcuate distal end of the guidewire for improved tracking.

SUMMARY OF THE INVENTION

The present invention relates generally to the field of intravascular guidewires. More particularly, the present invention pertains to intravascular guidewires having an articulating distal section. In one embodiment of the present invention, a guidewire having an articulating distal section is comprised of an elongated core wire having a longitudinal axis, a proximal end and a distal end; and an actuatable tip disposed about the distal end of the core wire having an outwardly expandable portion adapted to have a reduced profile in a first position, and an enlarged profile in a second position. The expandable portion of the actuatable tip may comprise a plurality of openings circumferentially disposed about the length of a tubular member. The outer diameter of the tubular member may be adapted to permit an intravascular device such as a cartridge filter to slide thereon.

In another embodiment of the present invention, a guidewire having an articulating distal section includes an elongated core wire having a longitudinal axis, a proximal end and a distal end; an actuator moveable about the core wire; and an actuatable tip adapted to have a reduced profile in a first position, and an enlarged profile in a second position. In one implementation of the present invention, the actuatable tip may include a spring coil helically disposed about the core wire. In another exemplary implementation, the actuatable tip may include a mesh sleeve adapted to outwardly expand when compressed axially. In yet another exemplary implementation, the actuatable tip may include an accordion-shaped polymeric tube similarly adapted to outwardly expand when compressed axially.

In another embodiment, the distal section of an articulating guidewire includes a friction fit between the core wire and the actuatable tip which can be utilized to prevent the distal section of the guidewire from reverting to the first position, once articulated. Alternatively, a locking mechanism such as a locking hub can be utilized to prevent the distal section of the guidewire from reverting to the first position, once articulated.

DETAILED DESCRIPTION OF THE INVENTION

The following detailed description should be read with reference to the drawings, in which like elements in different drawings are numbered in like fashion. Although examples of construction, dimensions, materials and manufacturing processes are illustrated for the various elements, those skilled in the art will recognize that many of the examples provided have suitable alternatives that may be utilized.

Figure 1:
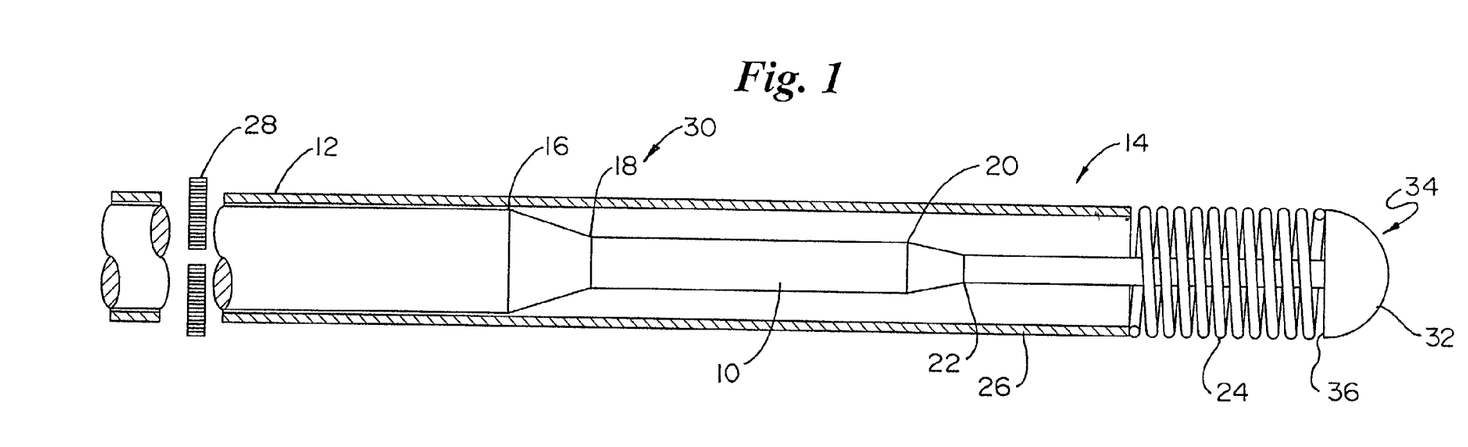
FIG. 1 is a plan view of an articulating guidewire in accordance with a first embodiment of the present invention.

FIG. 1 is a plan view of an articulating guidewire 30 in accordance with a first embodiment of the present invention. Guidewire 30 includes an elongated core wire 10 having a relatively stiff proximal section 12, and relatively flexible distal section 14. As shown in FIG. 1, core wire 10 has a relatively large profile on proximal section 12 which tapers to a smaller profile from point 16 to point 18, and again at point 20 to point 22. Core wire 10 may have any number of tapering sections disposed thereon without deviating from the scope of the invention. In one implementation of the present invention (not shown), core wire 10 may continuously taper from proximal section 12 to distal section 14.

Disposed on distal section 14 of core wire 10 is a wire tip 32. Wire tip 32 has a rounded distal end 34, and is generally circular in cross-sectional area. Wire tip 32 can be atraumatic for reduced tissue damage during advancement of the guidewire. Alternatively, wire tip 32 can be comprised of a substantially hard material.

In the particular embodiment of FIG. 1, guidewire 30 also includes a tubular member 26 and a spring coil 24, both moveable about distal section 14 of core wire 10. Tubular member 26 may have a length substantially similar to the length of core wire 10. Conversely, tubular member 26 may have a length substantially shorter than the length of core wire 10. In either implementation, the outer diameter of tubular member 26 is adapted to permit an intravascular device such as an embolic protection filter to slide thereon.

As discussed in greater detail below, spring coil 24 is adapted to have a reduced profile in a first position, and an enlarged profile in a second position. In the first (i.e. reduced profile) position, spring coil 24 has an outer diameter which is substantially similar to the outer diameter of tubular member 26, facilitating placement of guidewire 30 beyond a lesion or other protrusion within the vasculature with minimal interference. In the second (i.e. enlarged profile) position, spring coil 24 has an outer diameter greater than the outer diameter of tubular member 26, allowing spring coil 24 to function as a distal stop.

Also shown in the embodiment of FIG. 1 is a proximal locking hub 28. Proximal locking hub 28 is any suitable and any commercially available locking mechanism that can be configured to lock tubular member 26 to core wire 10.

Figure 2:
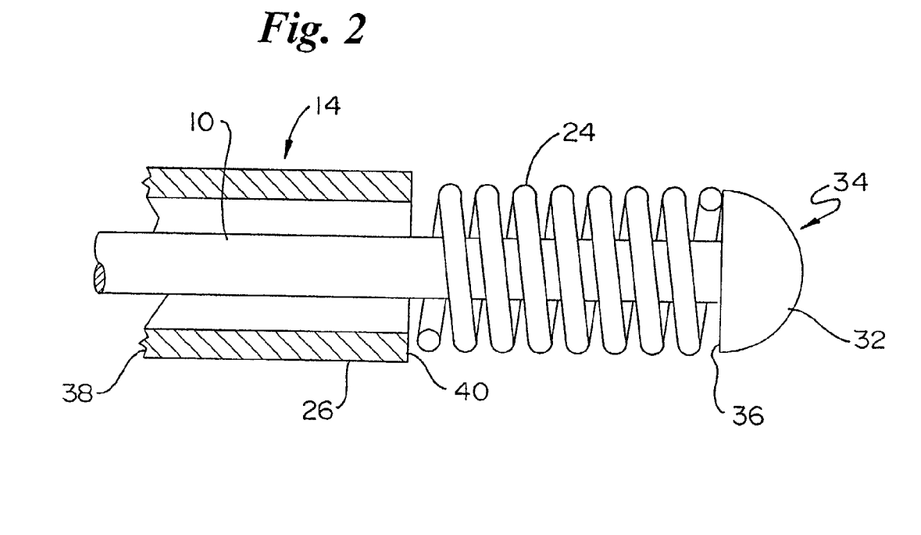
FIG. 2 is a cross-sectional view of the distal section of the guidewire in FIG. 1 showing the guidewire in a first position having a reduced profile.

FIG. 2 is a cross-sectional view of the distal section 14 of the guidewire illustrated in FIG. 1. Tubular member 26 has a proximal end (not shown) and a distal end 40. A shoulder 36 disposed on the proximal end of wire tip 32 is adapted to prevent tubular member 26 and spring coil 24 from sliding off the distal end of core wire 10.

Abutting the distal end 40 of tubular member 26, and the shoulder 36 of wire tip 32, is spring coil 24. In the embodiment shown in FIG. 2, spring coil 24 has one or more coils helically disposed about a portion of core wire 10. The distal end of spring coil 24 may be attached to the shoulder 36 of wire tip 32. Similarly, the proximal end of spring coil 24 may be attached to the distal end 40 of tubular member 26. Attachment of spring coil 24 to either shoulder 36 or tubular member 24 may be accomplished by solder, braze, adhesive or any other suitable attachment means.

Figure 3:
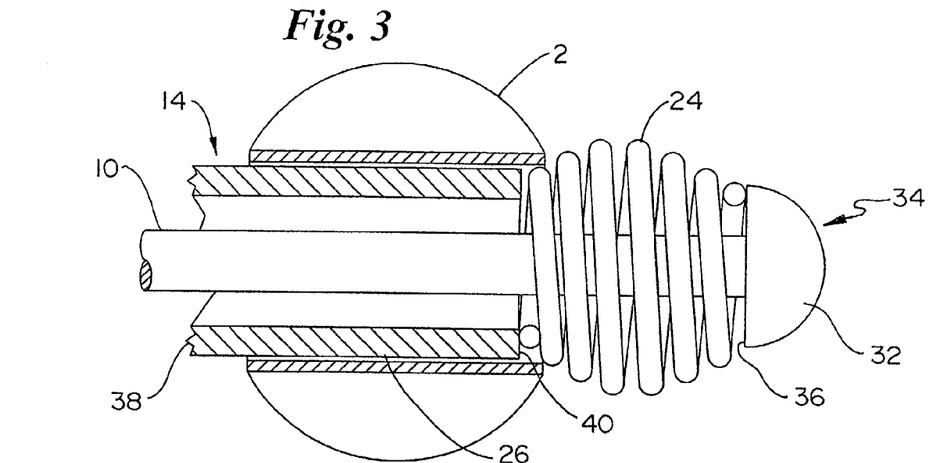
FIG. 3 is another cross-sectional view of the distal section of the guidewire in FIG. 1 showing the guidewire in a second position having an enlarged profile.

In use, guidewire 30 can be inserted through a guide catheter into the body and placed at a desired location distal a lesion. Tubular member 26 is then advanced distally, as shown in FIG. 3, causing spring coil 24 to compress axially and expand in an outward direction to form a distal stop. Once the guidewire is in position and the distal stop is engaged, a embolic protection filter 2 can then be advanced to a desired location along the guidewire to capture embolic debris dislodged during the procedure.

While the particular embodiment shown in FIG. 3 illustrates the actuation of spring coil 24 by advancing tubular member 26 distally, it is to be recognized that other methods to actuate the distal stop may be utilized. For example, tubular member 26 may be rotated about its major axis in either a clockwise or counter-clockwise direction, depending on the disposition of the coils, causing spring coil 24 to expand radially and form a distal stop. In another exemplary implementation, a friction fit between the inner diameter of filter 2 and the outer diameter of tubular member 26 can be utilized to actuate spring coil 24. In use, the frictional force resulting from the distal movement of filter 2 about tubular member 26 causes tubular member 26 to advance distally and compress spring coil 24 axially, thus forming a distal stop.

To prevent tubular member 26 from sliding proximally once the distal section 14 of the guidewire has been articulated, a friction fit between the inner diameter of tubular member 26 and the outer diameter of core wire 10 can also be utilized as an alternative to proximal locking hub 28. This frictional fit is adapted to permit motion of the tubular member 26 along core wire 10 only when a sufficient force is applied to tubular member 26 by the physician.

Figure 4:
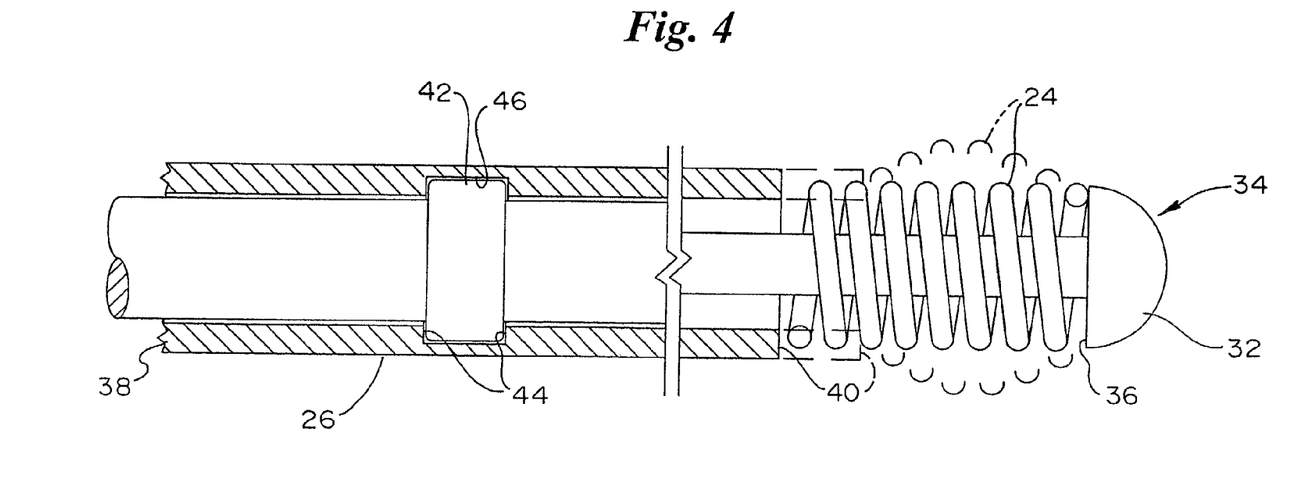
FIG. 4 is cross-sectional view of a particular implementation of the present invention employing a locking mechanism on the distal section of the guidewire.

In addition to the frictional fit between core wire 10 and tubular member 26, or the locking hub 28 described with respect to FIG. 1, a locking mechanism can be employed on the guidewire to prevent undesired movement of spring coil 24, once guidewire 30 has been articulated. As illustrated in the exemplary embodiment of FIG. 4, the locking mechanism can be comprised of an enlarged outer diameter section 42 disposed on core wire 10 corresponding in size and shape to a reduced inner diameter portion 44 disposed on tubular member 26. When tubular member 26 is advanced distally, as shown in FIG. 4, the enlarged diameter section 42 locks into the reduced inner diameter section 44, thereby preventing tubular member 26 from retracting proximally.

Although the use of a frictional fit and/or locking mechanism are described with respect to the exemplary embodiments illustrated in FIGS. 1–4, these features are not limited to those embodiments. Instead, a frictional fit and/or locking mechanism may be utilized in conjunction with any embodiment to prevent the tip from reverting to a collapsed position once the guidewire has been articulated.

Figure 5:
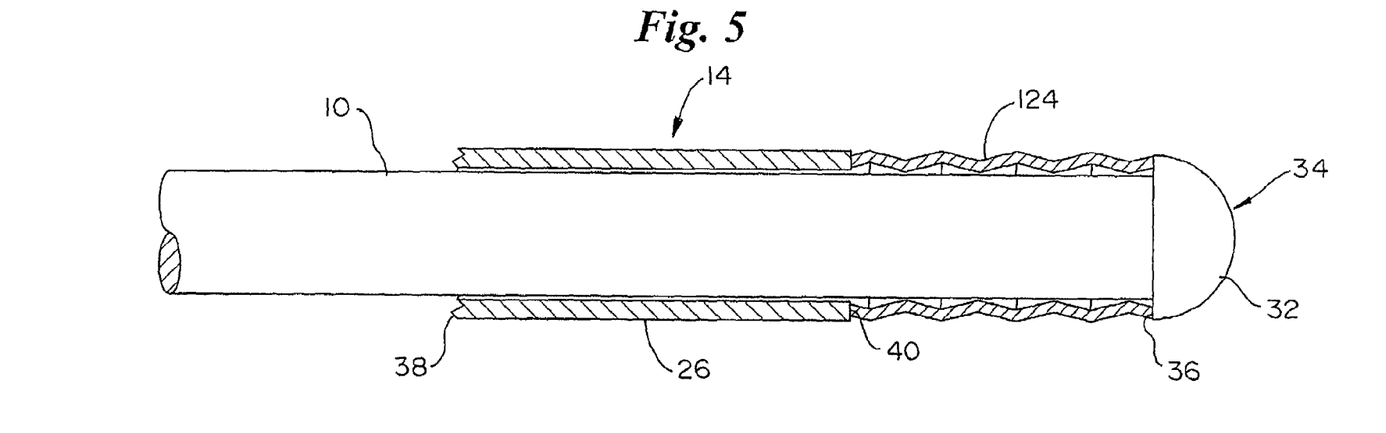
FIG. 5 is a cross-sectional view of the distal section of an articulating guidewire in accordance with a second embodiment of the present invention, wherein the guidewire is shown in a first position having a reduced profile.
Figure 6:
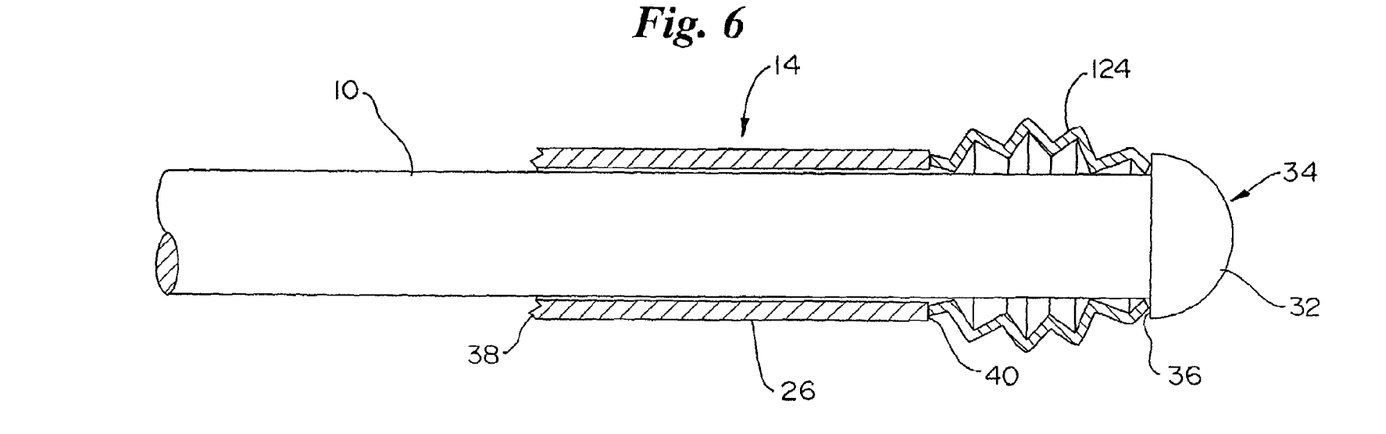
FIG. 6 is another cross-sectional view of the guidewire in FIG. 5 showing the distal section of the guidewire in a second position having an enlarged profile.

FIGS. 5 and 6 are cross-sectional views of the distal section 114 of an articulating guidewire in accordance with an additional embodiment of the present invention. As shown in FIG. 5, an accordion-shaped polymeric tube 124 can be utilized as a distal stop when actuated by a tubular member 126. Polymeric tube 124 can be attached proximally to distal end 140 of tubular member 126, and distally to shoulder 136 of wire tip 132.

As shown in FIG. 6, once the guidewire is advanced to a desired location within the body, tubular member 126 is advanced distally, forcing polymeric tube 124 to compress axially and expand in an outward direction. A embolic protection filter can then be advanced along tubular member 126 until the distal end of the filter abuts a portion of the outwardly expanded polymeric tube 124.

Figure 7:
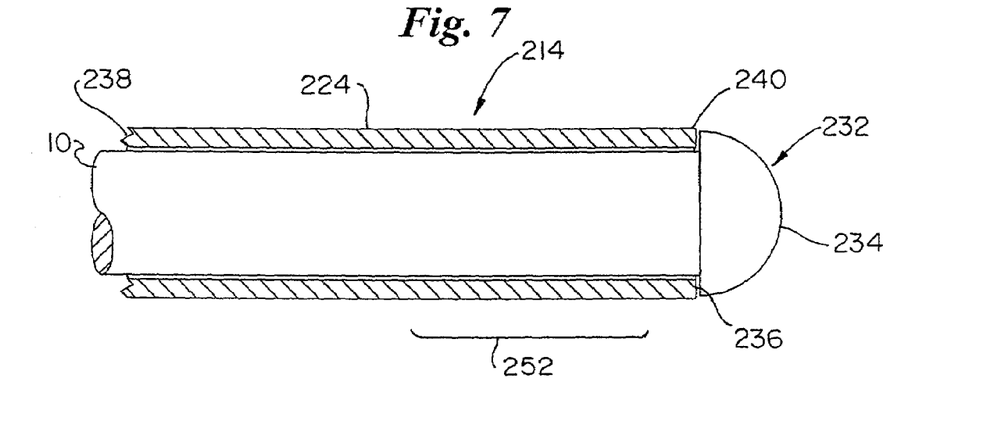
FIG. 7 is a cross-sectional view of the distal section of an articulating guidewire in accordance with a third embodiment of the present invention, wherein the guidewire is shown in a first position having a reduced profile.
Figure 8:
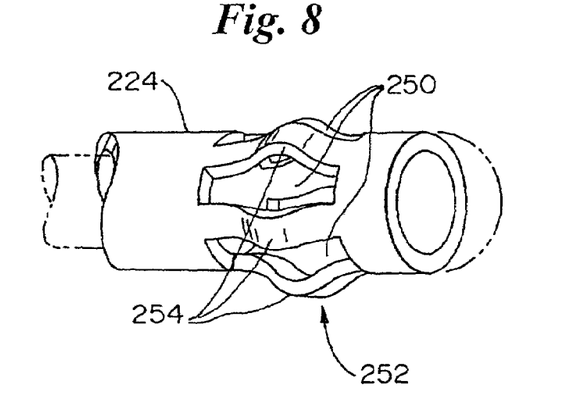
FIG. 8 is a plan view of the guidewire in FIG. 7 showing a plurality of openings circumferentially disposed about a distal section of the guidewire.
Figure 9:
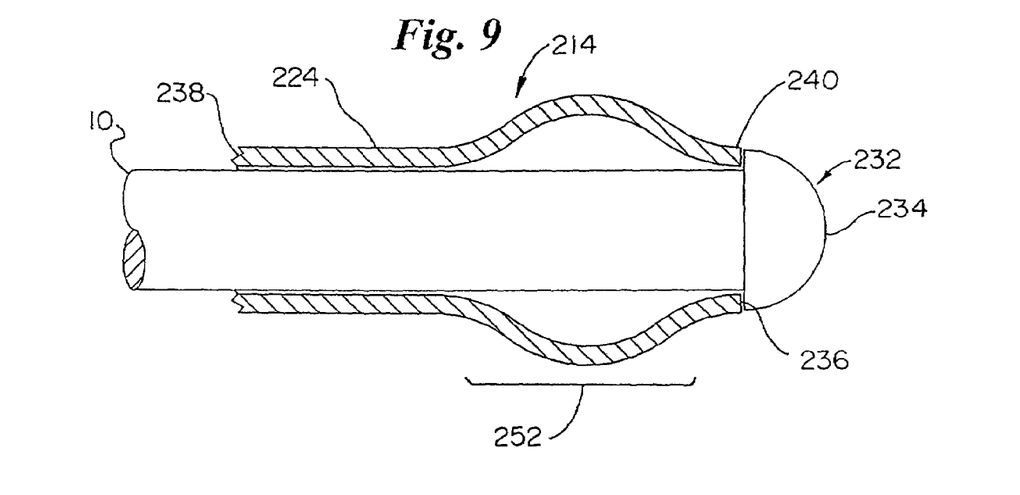
FIG. 9 is another cross-sectional view of the guidewire in FIG. 7 showing the distal section of the guidewire in a second position having an enlarged profile.

FIGS. 7–9 illustrate yet another exemplary embodiment in accordance with the present invention. A tubular member 224 having a proximal end 238 and a distal end 240 is moveable about core wire 10. Tubular member 224 includes a distal section 252 which expands outwardly when compressed axially.

As shown in greater detail in FIG. 8, distal section 252 includes a plurality of openings 250 circumferentially disposed about tubular member 224. The supports 254 between the openings 250, in turn, are biased to displace in an outward direction when compressed axially. As illustrated in FIG. 9, when tubular member 224 is advanced distally against the shoulder 236 of wire tip 232, the supports 254 are compressed axially and displace in an outward direction, creating a distal stop.

Figure 10:
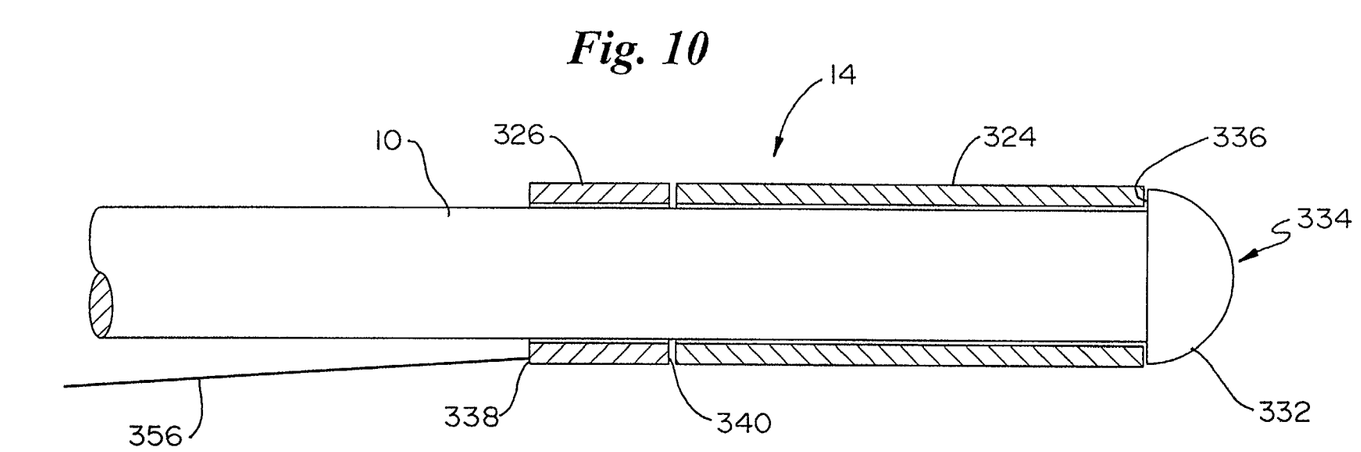
FIG. 10 is a cross-sectional view of a distal section of an articulating guidewire in accordance with a fourth embodiment of the present invention, wherein the guidewire is shown in a first position having a reduced profile.
Figure 11:
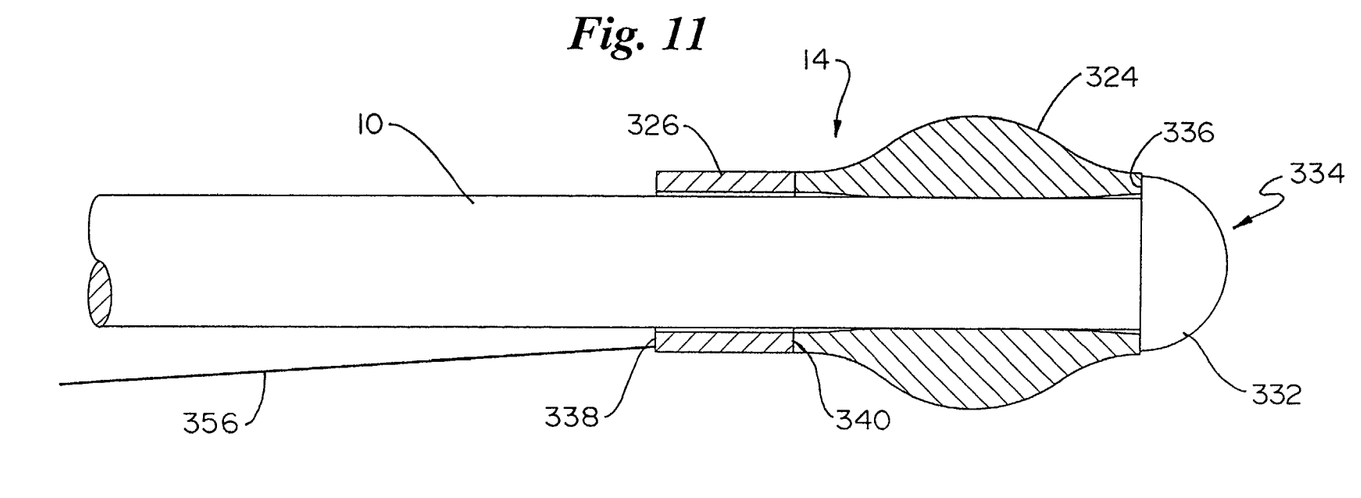
FIG. 11 is another cross-sectional view of the guidewire in FIG. 10 showing the distal section of the guidewire in a second position having an enlarged profile.

FIGS. 10 and 11 show another exemplary embodiment in accordance with the present invention. In the exemplary embodiment of FIG. 10, an articulating guidewire is comprised of an elongated core wire 10, a tubular segment 326 having proximal end 338 and distal end 340, an actuatable tip 324, and a wire tip 332. A portion of tip 324 is y adapted to expand in an outward direction when tubular segment 326 is advanced distally against the proximal end thereof. Tip 324 may be comprised of any number of suitable polymeric materials such as polyethylene or polystyrene.

In the particular embodiment of FIG. 10, an axially stiff pushing member 356 having a handle (not shown) disposed proximally thereof is shown attached to the proximal end 338 of tubular segment 326. To articulate the distal section of the guidewire, the operator advances tubular segment 326 distally against tip 324 with the aid of pushing member 356, causing tip 324 to expand in the outward direction, as shown in FIG. 11.

Figure 12:
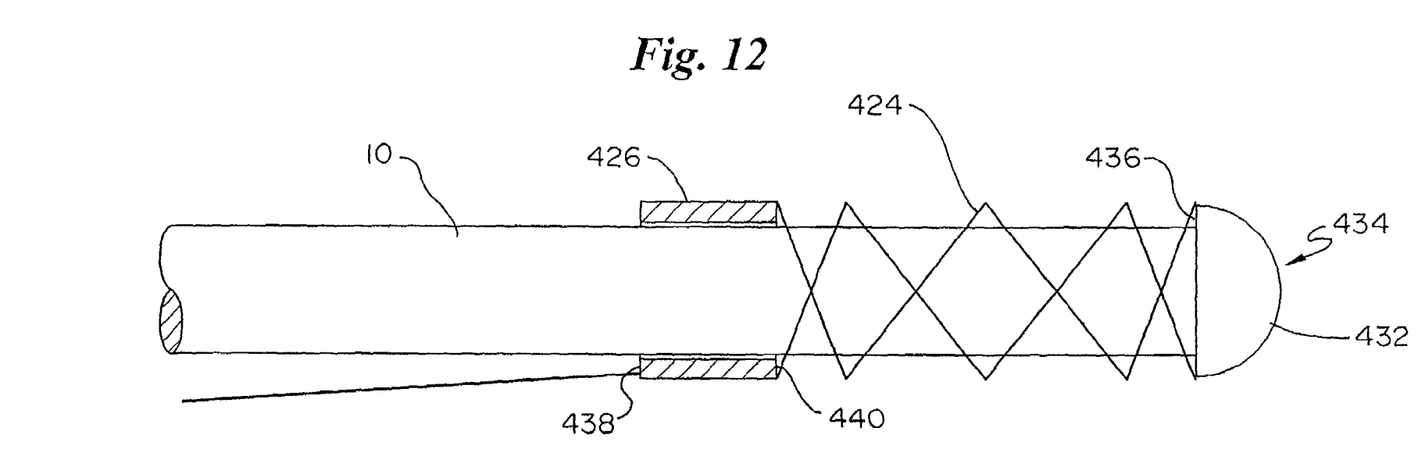
FIG. 12 is a cross-sectional view of a distal section of an articulating guidewire in accordance with a fifth embodiment of the present invention, wherein the guidewire is shown in a first position having a reduced profile.
Figure 13:
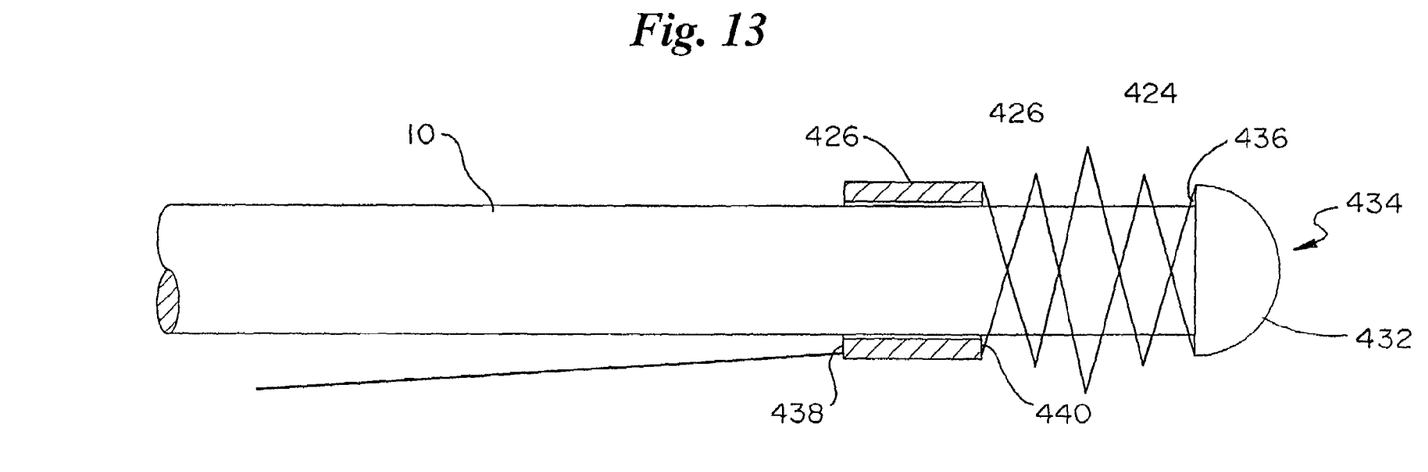
FIG. 13 is another cross-sectional view of the guidewire in FIG. 12 showing the distal section of the guidewire in a second position having an enlarged profile.

FIGS. 12 and 13 illustrate yet another embodiment in accordance with the present invention employing a mesh sleeve. As shown in FIG. 12, the distal section 414 of an articulating guidewire comprises an elongated core wire 10, a tubular segment 426 having a proximal end 438 and distal end 440, a wire tip 432, and an expandable mesh sleeve 424.

The mesh sleeve 424 can be attached proximally to distal end 440 of tubular segment 426, and distally at proximal end 436 of wire tip 432. The mesh sleeve is adapted to expand outwardly when compressed axially. Mesh sleeve 424 can be comprised of any suitable material(s) such as DACRON, which is available from E. I. du Pont de Nemours and Company in Wilmington, Del. DACRON is a synthetic polyester material used in many medical procedures for its strength and biocompatibility.

As illustrated in FIG. 13, once the guidewire is in a desired position within the body, the operator can advance tubular segment 426 distally, causing the mesh sleeve 424 to expand outwardly to form a distal stop along the guidewire. As with any of the previous embodiments, a frictional fit and/or locking mechanism can be utilized to prevent proximal motion of tubular member 426 once the mesh sleeve has been expanded to the second position.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood, however, that this disclosure is, in many respects, only illustrative. Changes may be made in details, particular in matters of shape, size and arrangement of parts without exceeding the scope of the invention.

What is claimed is:

1. An articulating guidewire, comprising:
   an elongated core wire having a longitudinal axis, a proximal end and a distal end;
   an actuatable stop disposed at the distal end of said core wire, said actuatable stop moveable between a collapsed position and an expanded position the stop having a first diameter in the expanded position;
   an actuator positioned adjacent the stop, said actuator moveable between a first position and a second position to move the stop between the collapsed position and the expanded position; and
   a filter slidably disposed on the core wire proximally of said actuatable stop the filter having an expanded position with a second diameter, the second diameter being larger than the first diameter, allowing fluids that flow through the filter to flow around the stop.

2. The guidewire of claim 1, wherein said actuatable stop comprises a tubular member having a proximal end and a distal end.

3. The guidewire of claim 2, wherein the distal section of said tubular member includes a plurality of circumferentially disposed openings adapted to permit a plurality of struts disposed therebetween to expand in an outward direction.

4. The guidewire of claim 2, wherein the inner diameter of said tubular member is substantially similar to the outer diameter of the core wire.

5. The guidewire of claim 2, wherein the inner diameter of said tubular member is larger than the outer diameter of the core wire.

6. The guidewire of claim 1, further comprising a locking mechanism adapted to prevent relative motion between the actuatable stop and the core wire.

7. The guidewire of claim 6, wherein the locking mechanism comprises an enlarged outer diameter portion disposed on the core wire.

8. The guidewire of claim 6, wherein the locking mechanism comprises an enlarged outer diameter portion disposed on the core wire corresponding in size and shape to a reduced inner diameter portion disposed on the actuatable stop.

9. The guidewire of claim 6, wherein the locking mechanism comprises a locking hub disposed about a proximal portion of the core wire.

10. The guidewire of claim 1, wherein the actuator contacts the actuatable stop, causing the actuatable stop to move between contracted and expanded positions.

11. The guidewire of claim 10, wherein the actuator has proximal and distal ends, and the distal end of the actuator contacts the actuatable stop.

12. An articulating guidewire, comprising:
    an elongated core wire having a longitudinal axis, a proximal end and a distal end;
    an actuatable stop disposed at the distal end of said core wire, said actuatable stop moveable between a collapsed position and an expanded position;
    an actuator disposable about the core wire, said actuator having a proximal end and a distal end; and
    a filter slidably disposed on the core wire proximally of said actuatable stop.

13. The guidewire of claim 12, wherein said actuatable stop comprises a spring coil.

14. The guidewire of claim 12, wherein said actuatable stop comprises a spring coil helically disposed about the core wire.

15. The guidewire of claim 12, wherein said actuatable stop comprises a polymeric tube.

16. The guidewire of claim 15, wherein said polymeric tube is accordion-shaped.

17. The guidewire of claim 12, wherein said actuatable stop comprises a mesh sleeve.

18. The guidewire of claim 17, wherein said mesh sleeve comprises a synthetic polyester material.

19. The guidewire of claim 12, wherein the inner diameter of the actuator is substantially similar to the outer diameter of the core wire.

20. The guidewire of claim 12, wherein the inner diameter of the actuator is larger than the outer diameter of the core wire.

21. The guidewire of claim 12, further comprising a locking mechanism adapted to prevent proximal motion of the actuator relative to the core wire.

22. The guidewire of claim 21, wherein the locking mechanism comprises an enlarged outer diameter portion disposed on the core wire.

23. The guidewire of claim 21, wherein the locking mechanism comprises an enlarged outer diameter portion disposed on the core wire corresponding in size and shape to a reduced inner diameter portion disposed on the actuator.

24. The guidewire of claim 21, wherein the locking mechanism comprises a locking hub disposed about a proximal portion of the core wire.

25. A method for placing an articulating guidewire in the vasculature, comprising the steps of:
  providing an articulating guidewire comprising an elongated core wire having a longitudinal axis, a proximal end and a distal end; an actuatable stop disposed at the distal end of the core wire, and an actuator positioned adjacent the actuatable stop, said actuator moveable between first and second positions, wherein moving the actuator between the first and second positions causes the actuatable stop to move between a collapsed position and an expanded position, and wherein the actuator has a first diameter in the expanded position;
  inserting the guidewire into the lumen of a blood vessel;
  positioning a distal portion of the guidewire beyond a lesion or other protrusion within the body;
  actuating the actuatable stop from the collapsed position to the expanded position; and
  advancing a filter on the guidewire to the stop, the filter having an expanded position with a second diameter, the second diameter being larger than the first diameter allowing fluids that flow through the filter to flow around the stop.

26. The method in accordance with claim 25, further comprising the step of advancing an intravascular device along the core wire until the intravascular device abuts the outwardly expanded stop.

27. A method for placing an articulating guidewire in the vasculature, comprising the steps of:
  providing an articulating guidewire comprising an elongated core wire having a longitudinal axis, a proximal end and a distal end; an actuatable stop disposed at the distal end of the core wire, said actuatable stop moveable between a collapsed position and an expanded position; and an actuator moveable about the core wire, said actuator having a proximal end and a distal end;
  inserting the guidewire into the lumen of a blood vessel;
  positioning a distal portion of the guidewire beyond a lesion or other protrusion within the body;
  actuating the stop from the collapsed position to the expanded position; and
  advancing a filter on the guidewire.

28. The method in accordance with claim 27, further comprising the step of advancing an intravascular device along the guidewire until the intravascular device abuts the outwardly expanded stop.

29. The method in accordance with claim 27, wherein the actuator is coupled to the actuatable stop.

* * * * *